(12) United States Patent
Shukla et al.

(10) Patent No.: US 8,419,939 B2
(45) Date of Patent: Apr. 16, 2013

(54) MICRO DIALYZER

(76) Inventors: Ashok Kumar Shukla, Ellicott City, MD (US); Mukta Misra Shukla, Ellicott City, MD (US); Kavita Misra Shukla, Ellicott City, MD (US)

( * ) Notice: Subject to any disclaimer, the term of this patent is extended or adjusted under 35 U.S.C. 154(b) by 399 days.

(21) Appl. No.: 12/583,680

(22) Filed: Aug. 25, 2009

(65) Prior Publication Data

US 2010/0044294 A1 Feb. 25, 2010

Related U.S. Application Data

(60) Provisional application No. 61/189,861, filed on Aug. 25, 2008.

(51) Int. Cl.
*B01D 63/00* (2006.01)
*B01D 35/30* (2006.01)

(52) U.S. Cl.
USPC ... 210/321.6; 210/121; 210/232; 210/321.84; 210/500.21; 422/547; 422/560; 422/565

(58) Field of Classification Search .................. 210/121, 210/232, 242.1, 321.6, 321.84, 500.21, 513; 422/547, 560, 565
See application file for complete search history.

(56) References Cited

U.S. PATENT DOCUMENTS

| | | | | |
|---|---|---|---|---|
| 4,450,076 A | * | 5/1984 | Medicus et al. | 210/242.1 |
| 4,964,961 A | * | 10/1990 | Brautigam et al. | 204/465 |
| 5,833,927 A | * | 11/1998 | Raybuck et al. | 422/513 |
| 6,458,275 B1 | * | 10/2002 | Shukla et al. | 210/321.6 |

* cited by examiner

*Primary Examiner* — John Kim

(57) ABSTRACT

A spherical dialysis chamber with a heavier cap (the density of cap material is higher than that of the dialyzer) or the distribution of weight is such that it is higher weight distribution is towards the cap, so that it tilts always towards the bottom of the container containing the dialysis buffer.

6 Claims, 3 Drawing Sheets

MICRO DIALYZER

This application (Applicants) claims the benefit of priority dated Aug. 25, 2008 of provisional application No. 61/189,861

FIELD OF THE INVENTION

In the present invention, we describe a device for the dialysis of small samples for the separation of small molecules from large molecules. The device has a chamber to contain the solution to be dialyzed, a membrane barrier and a cap to hold the membrane in place so that the dialysis chamber is separated from the dialysis solution through a membrane. The device is of such a shape that when it is placed in liquid, the membrane should be in contact with solution on both sides. To achieve this goal, we have developed a spherical dialysis chamber with a heavier cap (the density of cap material is higher than that of the dialyzer) or the distribution of weight is such that it is higher towards the cap, so that it tilts always towards the bottom of the container containing the dialysis buffer. One can also use a lightweight attachment so that the device swims in such a way that the membrane is always in contact with the inside and outside solution.

BACKGROUND OF THE INVENTION

Definitions

Dialysis Chamber: is a solid chamber, which contains a sample in the form of a solution.
Membrane: is semi-permeable membrane which allows certain molecular weight molecules to pass through, the molecules that are larger then the pore size of the membrane will be retained in the dialysis chamber.
Dialysis solution: A solution or water or buffer against which the dialysis is performed.
Sample (analytes): means any sample from a chemical or biological source and the sample may contain several molecules. Sample preparation means the purification and separation of different molecules in the sample.
Solvent: means organic and inorganic solvents including water, buffers, solutions.
Solute: means a liquid, solid or semi solid dissolved in the solvent.

BACKGROUND

Small sample preparation is typically performed to concentrate and/or to clean up samples by removing impurities such as detergent, salt or other molecules, prior to performing sample analysis by different analytical tools such as HPLC, Mass spectrometry, electrophoresis. The present invention describes a system using a dialysis membrane and a unique device for small sample preparation, concentration, as well as separation of different components comprising a sample.

Dialysis is routinely used in the biochemistry lab for desalting or removal of small molecules from a sample solution. Membranes of different Molecular Weight Cut Offs (MWCO) are available to separate biomolecules of a particular molecular weight. Different dialysis devices are currently available in the market.

In most of the commercially available dialysis devices, when the dialysis chamber is placed in the buffer, care has to be taken to place the chamber in such a way that the membrane is completely covered by the inside and outside solution. However, when the inside chamber is not completely filled, it is possible that the membrane surface is not fully covered with the sample solution or an air bubble develops, thus delaying the dialysis. Therefore, precaution is always needed while placing the dialysis chamber upside down in the buffer solution so that the membrane surface is covered with the sample. During the course of dialysis, when we place a magnetic stirrer in the container containing the buffer to stir the solution, the dialysis chamber may change its position and the membrane surface may not be in complete contact with the sample.

Here, we describe a dialysis chamber, which is of such a shape that when it is placed in the dialysis buffer, the dialysis membrane will always be fully covered with the sample and buffer solutions. This helps to speed up the dialysis as well as reduce the risk that some samples are not dialyzed.

The various features of novelty, which characterize the present invention, are pointed out with particularity in the claims annexed to and forming a part of this disclosure. For a better understanding of the invention, its advantages and objects, reference is made to the accompanying drawings and descriptive matter in which a preferred embodiment of the invention is illustrated.

BRIEF DESCRIPTION OF THE DRAWINGS

The foregoing and still other objects of this invention will become apparent, along with various advantages and features of novelty residing in the present embodiments, from study of the following drawing, in which.

DESCRIPTION OF THE PREFERRED EMBODIMENTS

Figure 1:
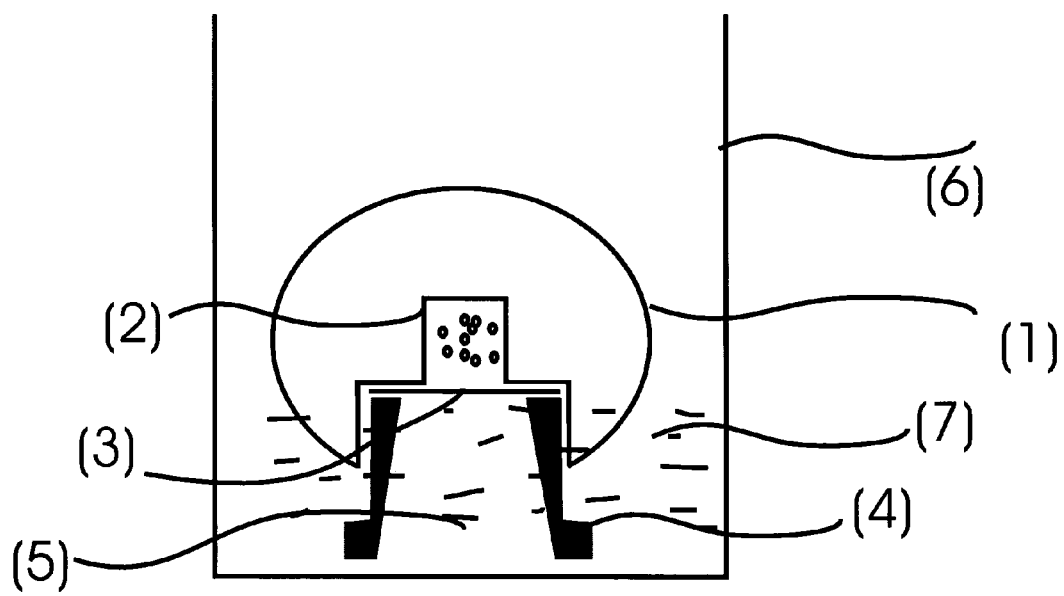
FIG. 1. is an expanded view of one embodiment of a dialyzer in spherical shape.
Figure 2:
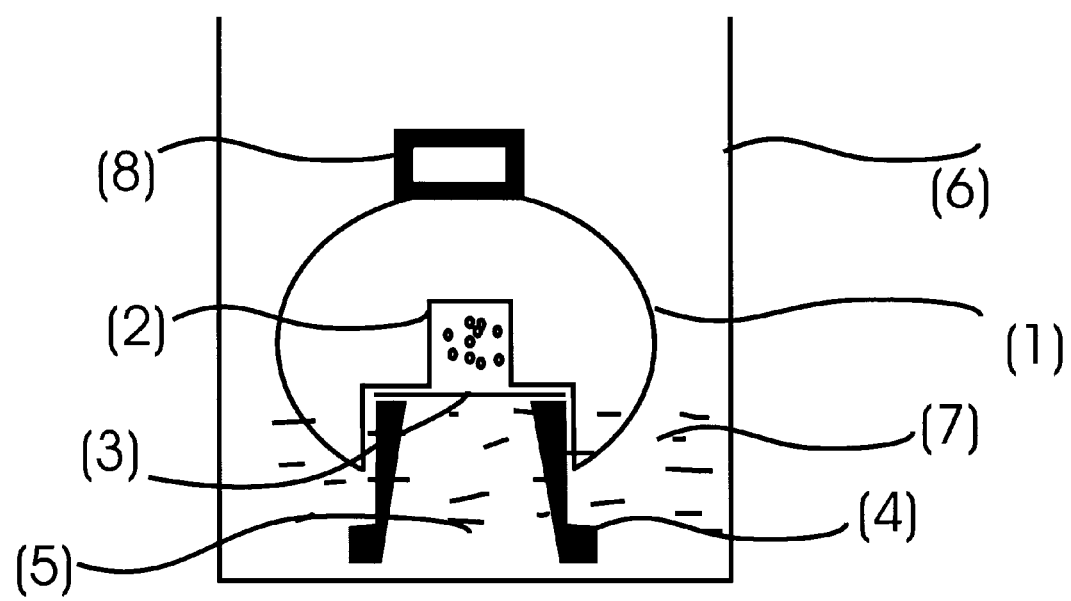
FIG. 2. is an expanded view of one embodiment of a dialyzer in spherical shape with lightweight attachment.

Referring to the drawings, FIG. 1 shows a spherical chamber (1) containing a dialysis cavity, hole or chamber (2), a membrane (3) and a cap (4) to hold the membrane (3) in place in such a way that small molecular weight (MW) molecules can pass through the particular MWCO membrane and larger MW molecules remain in the dialysis chamber (2). The cap (4) has a through hole (5) to get the membrane contact with the outer liquid (7) The dialysis device (1) can be spherical or of such a shape that when the device (1) along with the sample, cap and membrane is placed in a container with the buffer solution (6,) it tilts and is in complete contact with the outer dialysis buffer (7).

Figure 3:
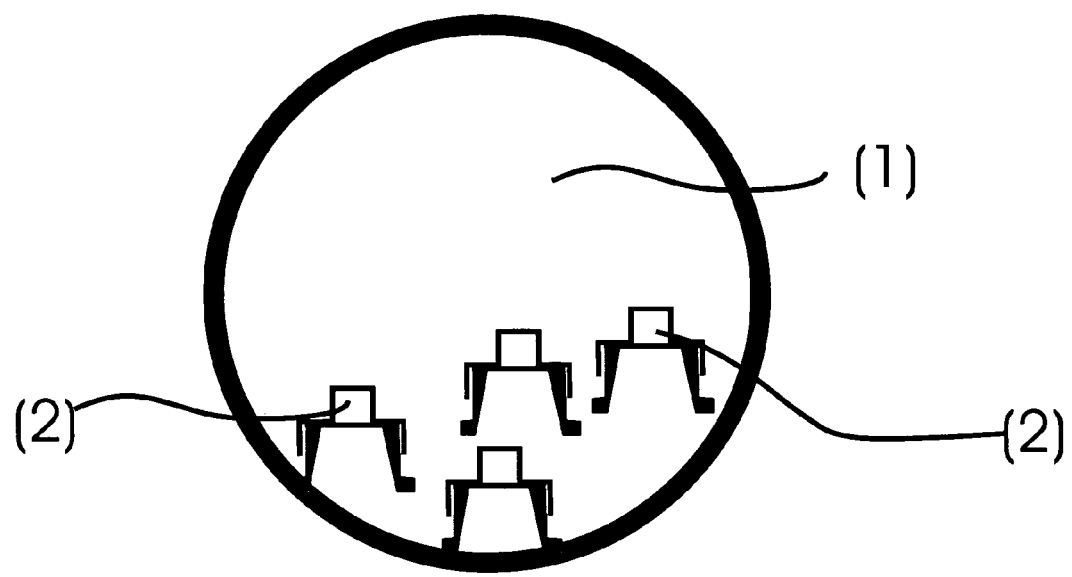
FIG. 3. is an expanded view of one embodiment of a dialyzer in spherical shape with multiple dialysis chambers.

The device (1) optionally can have more then one chamber (1) FIG. 3.

By adding or attaching a piece (8) made of the material, which has a lower density than the chamber (1), the whole chamber (1) will float fully or partially in the solution (7).

Otherwise, the chamber (1) can also be made of a material which can float in the solution (7).

The dialyzer (1) or cap (4) can be made of any plastic, such as polytetrafluoroethylene; polysulfone; polyethersulfone; cellulose acetate; polystyrene; polystyrene/acrylonitrile copolymer; PVDF; natural polymer; synthetic polymer; polymer; glass; plastic; fabric; paper; metallic; non-metallic; magnetic non-magnetic; and, combinations thereof. The cap (4) can be made of same or different material than the dialyzer (1).

The said membrane (3) is made of cellulose, modified cellulose or polymer.

This new dialyzer can be used for the sample preparation applications such as HPLC; mass spectrometry; MALDI; electrophoresis; qualitative and quantitative analytical methods.

This new dialyzer can be used in the sample preparation process performed for applications from the group consisting of purification of proteins, peptides, DNA and other biomolecules, size-based separation of molecules, chemical properties based separation of sample components, physical properties based separation of sample components.

EXAMPLE

A 10,000 Daltons dialysis membrane circle was used to dialyze a sample contains phosphate buffer and bovine serum albumin (BSA) (MW 65,000. After using the spherical dialyzer the content of the dialysis chamber was analyzed by High Performance Liquid Chromatography (HPLC) and compared with normal dialysis method. The phosphate buffer was removed from the dialysis tubing and only BSA was left in the dialysis tubing.

While a specific embodiment of the invention has been shown and described in detail to illustrate the application of the principles of the invention, it is understood that the invention may be embodied otherwise without departing from such principles and that various modifications, alternate constructions, and equivalents will occur to those skilled in the area given the benefit of this disclosure and the embodiment described herein, as defined by the appended claims.

What is claimed is:

1. A micro dialysis device of a sphere like geometry comprising a chamber, a dialysis membrane and a through hole cap, wherein said membrane is placed between said chamber and said through hole cap, said chamber contains cavity or hole, said cavity contains a sample solution containing different molecular weight molecules, when such a chamber is placed in the liquid it will tilt in a way favorable for dialysis.

2. A device as in claim 1, wherein material of said chamber is selected from the group consisting of polytetrafluoroethylene; polysulfone; polyethersulfone; cellulose acetate; polystyrene; polystyrene/acrylonitrile copolymer; PVDF; natural polymer; synthetic polymer; polymer; glass; plastic; fabric; paper; metallic; non-metallic; magnetic non-magnetic; and, combinations thereof.

3. A device as in claim 1, wherein material of said cap is selected from the group consisting of polytetrafluoroethylene; polysulfone; polyethersulfone; cellulose acetate; polystyrene; polystyrene/acrylonitrile copolymer; PVDF; natural polymer; synthetic polymer; polymer; glass; plastic; fabric; paper; metallic; non-metallic; magnetic non-magnetic; and, combinations thereof.

4. A device as in claim 1 wherein said membrane is range of different molecular weight cut off's (MWCO) from 100 daltons to 100 million daltons.

5. A device as in claim 1 wherein said chamber contains more than one sample chamber.

6. A device as in claim 1, wherein the said membrane is made of cellulose, modified cellulose or polymer.

* * * * *